US006169074B1

(12) United States Patent
Montal et al.

(10) Patent No.: US 6,169,074 B1
(45) Date of Patent: Jan. 2, 2001

(54) PEPTIDE INHIBITORS OF NEUROTRANSMITTER SECRETION BY NEURONAL CELLS

(75) Inventors: Mauricio Montal, La Jolla; Jaume M. Canaves, San Diego, both of CA (US); Antonio V. Ferrer-Monteil, Alicante (ES)

(73) Assignee: The Regents of the University of California, Oakland, CA (US)

( * ) Notice: Under 35 U.S.C. 154(b), the term of this patent shall be extended for 0 days.

(21) Appl. No.: 08/819,286

(22) Filed: Mar. 18, 1997

Related U.S. Application Data

(63) Continuation-in-part of application No. 60/013,599, filed on Mar. 18, 1996.

(51) Int. Cl.[7] .......................... C07K 7/08; C07K 14/435; A61K 38/10; A61K 38/17

(52) U.S. Cl. ............................ 514/12; 530/324; 530/326; 514/13

(58) Field of Search ................................... 514/2, 12, 13; 530/300, 324, 326, 350

(56) References Cited

FOREIGN PATENT DOCUMENTS

95/32738 12/1995 (WO) .
95/33850 12/1995 (WO) .

OTHER PUBLICATIONS

Rudinger, In "Peptide Hormones" (ed. J.A. Parsons) University Park Press, Baltimore, pp. 1–7, 1976.*

Schiavo, et al, "Botulinum Neurotoxin Type C Cleaves a Single Lys–Ala Bond within the Carboxyl–terminal Region of Syntaxins"; Journal of Biological Chemistry, May 5, 1995, Vol. 270, No. 18, pp. 10566–10570.

Schiavo, et al., "Identification of the Nerve Terminal Targets of Botulinum Neurotoxin Serotypes A, D and E"; Journal of Biological Chemistry; Nov. 15, 1993, vol. 268, No. 32, pp. 23784–53787.

Yamasaki, et al., "Botulinum Neurotoxin Type G Proteolyses the $Ala^{81}$–$Ala^{82}$ Bond of Rat Synaptobrevin 2"; aBiochem. Biophys. Res. Comm., Apr. 29, 1994, vol. 200, No. 2, pp. 829–835.

Hayashi, et al., "Synaptic vesicle membrane fusion complex: action of clostridial neurotoxins on assembly"; EMBO Journal 1994, vol. 13, No. 21, pp. 5051–5061.

* cited by examiner

*Primary Examiner*—Gary L. Kunz
*Assistant Examiner*—Robert C. Hayes
(74) *Attorney, Agent, or Firm*—Foley & Lardner

(57) ABSTRACT

The invention consists of peptides which inhibit the secretion of neurotransmitters from synaptic vesicles. The peptides of the invention are believed to mimic the activity of neurotoxins produced by *Clostridium botulinum* and *tetani* (including botulinum serotypes A, B, C, D, E, F and G). Structurally, the peptides are comprised of amino acid fragments from the substrate binding domains selected from three proteins which bind to form a receptor for docking of synaptic vesicles to the plasma membranes of neuronal cells; i.e., SNAP-25, VAMP-2 and syntaxin. Certain of the inventive peptides exhibit strong inhibitory activity; e.g., 50% or greater decline in neurotransmitter release is obtained at even nanomolar concentrations. The peptides are suited for use as substitutes for Clostridium neurotoxins in clinical applications and in compounds for targeted delivery of drugs into neural cells.

10 Claims, 6 Drawing Sheets

SNAP-25 ESUPS

```
                                    BoNT/E              BoNT/A
1                        170          ↓                   ↓       206
[▓▓▓▓▓▓▓▓▓▓▓▓▓▓▓▓▓▓▓▓▓▓▓▓EIDTQNRQIDRIMEKADSNKTRIDEANQRATKMLGSG]

[EIDTQNRQIDRIMEKADSNKTRIDEANQRATKMLGSG]
                              [ ESUP/A20h ]
         [ ESUP/E20h ]                    [ESUP/A7h]
           [ ESUP/E16h ]                    [ ESUP/A12h ]
             [ ESUP/E12h ]                    [ ESUP/A9h ]
                    [    ESUP/E26h    ]
```

```
MAEDADMRNE  LEEMQRRADQ  LADESLESTR  RMLQLVEESK  DAGIRTLVML  DEQGEQLERI
EEGMDQINKD  MKEAEKNLTD  LGKFCGLCVC  PCNKLKSSDA  YKKAWGNNQD  GVVASQPARV
VDEREQMAIS  GGFIRRVTND  ARENEMDENL  EQVSGIIGNL  RHMALDMGNE  IDTQNRQIDR
IMEKADSNKT  RIDEANQRAT  KMLGSG
```

Figure 3

MSATAATAPP AAPAGEGGPP APPPNLTSNR RLQQTQAQVD EVVDIMRVNV DKVLERDQKL
SELDDRADAL QAGASQFETS AAKLKRKYWW KNLKMMIILG VICAIILIII IVYFSS

SYNTAXIN-A ESUPS

```
                                              BoNT/C
1                              199       218  ↓   288
▓▓▓▓▓▓▓▓▓▓▓▓▓▓▓▓▓▓▓▓▓▓▓▓▓▓▓▓▓▓▓│HSEII...MFMD│▓▓▓
```

HSEIIKLENSIRELHDMFMD

ESUP/C28b
ESUP/C24b
ESUP/C20b
ESUP/C16b
ESUP/C12b

MKDRTQELRT AKDSDDDDDV TVTVDRDRFM DEFFEQVEEI RGFIDKIAEN VEEVKRKHSA
ILASPNPDEK TKEELEELMS DIKKTANKVR SKLKSIEQSI EQEEGLNRSS ALDRIRKTQH
STLSRKFVEV MSEYNATQSD YRERCKGRIO RQLEITGRTT TSEELEDMLE SGNPAIFASG
IIMDSSISKQ ALSEIETRHS EIIKLENSIR ELHDMFMDMA MLVESQGEMI DRIEYNVEHA
VDYVERAVSD TKKAVKYQSK ARRKKIMIII CCVILGIIIA STIGGIFG

Figure 5

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
       (A) LENGTH: 206 amino acids
       (B) TYPE: amino acid
       (C) STRANDEDNESS: Not Relevant
       (D) TOPOLOGY: linear (ii) MOLECULE TYPE: peptide (xi) SEQUENCE DESCRIPTION: SEQ ID NO:1:

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
                35                  40                  45

Met Leu Asp Glu Gln Gly Glu Gln Leu Glu Arg Ile Glu Glu Gly Met
            50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
                115                 120                 125

Ile Ser Gly Gly Phe Ile Arg Arg Val Thr Asn Asp Ala Arg Glu Asn
            130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190

Asp Glu Ala Asn Gln Arg Ala Thr Lys Met Leu Gly Ser Gly
                195                 200                 205
```

(2) INFORMATION FOR SEQ ID NO:2:

(i) SEQUENCE CHARACTERISTICS:
       (A) LENGTH: 116 amino acids
       (B) TYPE: amino acid
       (C) STRANDEDNESS: Not Relevant
       (D) TOPOLOGY: linear (ii) MOLECULE TYPE: peptide (xi) SEQUENCE DESCRIPTION: SEQ ID NO:2:

Met Ser Ala Thr Ala Ala Thr Ala Pro Pro Ala Ala Pro Ala Gly Glu

```
              1               5                  10                 15
Gly Gly Pro Pro Ala Pro Pro Asn Leu Thr Ser Asn Arg Arg Leu
                    20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
        50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Ser
            115
```

(2) INFORMATION FOR SEQ ID NO:3:

(i) SEQUENCE CHARACTERISTICS:
        (A) LENGTH: 288 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
                20                  25                  30

Phe Phe Glu Gln Val Glu Glu Ile Arg Gly Phe Ile Asp Lys Ile Ala
            35                  40                  45

Glu Asn Val Glu Glu Val Lys Arg Lys His Ser Ala Ile Leu Ala Ser
        50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
        130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
        210                 215                 220

Ser Gln Gly Glu Met Ile Asp Arg Ile Glu Tyr Asn Val Glu His Ala
```

```
                       225                 230                 235                 240
Val Asp Tyr Val Glu Arg Ala Val Ser Asp Thr Lys Lys Ala Val Lys
                    245                 250                 255
Tyr Gln Ser Lys Ala Arg Arg Lys Lys Ile Met Ile Ile Ile Cys Cys
                    260                 265                 270
Val Ile Leu Gly Ile Ile Ile Ala Ser Thr Ile Gly Gly Ile Phe Gly
                    275                 280                 285
```

(2) INFORMATION FOR SEQ ID NO:4:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Glu Ile Asp Thr Gln Asn Arg Gln Ile Asp Arg Ile Met Glu Lys Ala
1               5                   10                  15
Asp Ser Asn Lys Thr Arg Ile Asp Glu Ala Asn Gln Arg Ala Thr Lys
                20                  25                  30
Met Leu Gly Ser Gly
                35
```

(2) INFORMATION FOR SEQ ID NO:5:

(i) SEQUENCE CHARACTERISTICS:
        (A) LENGTH: 56 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Asn Arg Arg Leu Gln Gln Thr Gln Ala Gln Val Asp Glu Val Val Asp
1               5                   10                  15
Ile Met Arg Val Asn Val Asp Lys Val Leu Glu Arg Asp Gln Lys Leu
                20                  25                  30
Ser Glu Leu Asp Asp Arg Ala Asp Ala Leu Gln Ala Gly Ala Ser Gln
            35                  40                  45
Phe Glu Thr Ser Ala Ala Lys Leu
        50                  55
```

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
His Ser Glu Ile Ile Lys Leu Glu Asn Ser Ile Arg Glu Leu His Asp
1               5                   10                  15
Met Phe Met Asp
            20
```

(2) INFORMATION FOR SEQ ID NO:7:

(i) SEQUENCE CHARACTERISTICS:
    (A) LENGTH: 20 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:7:

Glu Ile Asp Thr Gln Asn Arg Gln Ile Asp Arg Ile Met Glu Lys Ala
1               5                   10                  15

Asp Ser Asn Lys
            20

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Ile Met Glu Lys Ala Asp Ser Asn Lys Thr Arg Ile Asp Glu Ala Asn
1               5                   10                  15

Gln Arg Ala Thr Lys Met Leu Gly Ser Gly
            20                  25

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

Ser Asn Lys Thr Arg Ile Asp Glu Ala Asn Gln Arg Ala Thr Lys Met
1               5                   10                  15

Leu Gly Ser Gly
            20

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

Thr Asp Ser Ser Gly Arg Glu Met Ile Lys Ala Asn Lys Gln Leu Ala
1               5                   10                  15

Asn Gly Thr Arg
            20

(2) INFORMATION FOR SEQ ID NO:11:

(i) SEQUENCE CHARACTERISTICS:
        (A) LENGTH: 10 amino acids (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:11:

Met Leu Asp Glu Gln Gly Gln Leu Glu Arg
1               5                   10

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

Gln Asn Arg Gln Ile Asp Arg Ile Met Glu Lys Ala Asp Ser Asn Lys
1               5                   10                  15

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

Ala Asp Ala Leu Gln Ala Gly Ala Ser Gln Phe Glu Thr Ser Ala Ala
1               5                   10                  15

Lys Leu Lys Arg
            20

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

Arg Asp Gln Lys Leu Ser Glu Leu Asp Asp Arg Ala
1               5                   10

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

Lys Val Leu Glu Arg Asp Gln Lys Leu Ser Glu Leu Asp Asp Arg Ala
1               5                   10                  15

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

Val Asn Val Asp Lys Val Leu Glu Arg Asp Gln Lys Leu Ser Glu Leu
1               5                   10                  15

Asp Asp Arg Ala
            20

(2) INFORMATION FOR SEQ ID NO:17:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:17:

Asp Ile Met Arg Val Asn Val Asp Lys Val Leu Glu Arg Asp Gln Lys
1               5                   10                  15

Leu Ser Glu Leu Asp Asp Arg Ala
            20

(2) INFORMATION FOR SEQ ID NO:18:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:18:

Asp Glu Val Val Asp Ile Met Arg Val Asn Val Asp Lys Val Leu Glu
1               5                   10                  15

Arg Asp Gln Lys Leu Ser Glu Leu Asp Asp Arg Ala
            20                  25

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:19:

Asp Glu Val Val Asp Ile Met Arg Val Asn Val Asp
1               5                   10

(2) INFORMATION FOR SEQ ID NO:20:

(i) SEQUENCE CHARACTERISTICS:
        (A) LENGTH: 16 amino acids
        (B) TYPE: amino acid
        (C) STRANDEDNESS: Not Relevant (D) TOPOLOGY: linear (ii) MOLECULE TYPE: peptide (xi) SEQUENCE DESCRIPTION: SEQ ID NO:20:

Gln Ala Gln Val Asp Glu Val Val Asp Ile Met Arg Val Asn Val Asp
1               5                   10                  15

(2) INFORMATION FOR SEQ ID NO:21:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:21:

Leu Gln Gln Thr Gln Ala Gln Val Asp Glu Val Val Asp Ile Met Arg
1               5                   10                  15

Val Asn Val Asp
            20

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:22:

Gln Gln Thr Gln Ala Gln Val Asp Glu Val Val Asp
1               5                   10

(2) INFORMATION FOR SEQ ID NO:23:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:23:

Asn Arg Arg Leu Gln Gln Thr Gln Ala Gln Val Asp Glu Val Val Asp
1               5                   10                  15

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

Asn Leu Thr Ser Asn Arg Arg Leu Gln Gln Thr Gln Ala Gln Val Asp
1               5                   10                  15

Glu Val Val Asp
            20

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:25:

```
Asn Ser Ile Arg Glu Leu His Asp Met Phe Met Asp
1               5                  10
```

(2) INFORMATION FOR SEQ ID NO:26:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:26:

```
Ile Lys Leu Glu Asn Ser Ile Arg Glu Leu His Asp Met Phe Met Asp
1               5                  10                  15
```

(2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:27:

```
His Ser Glu Ile Ile Lys Leu Glu Asn Ser Ile Arg Glu Leu His Asp
1               5                  10                  15
Met Phe Met Asp
            20
```

(2) INFORMATION FOR SEQ ID NO:28:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:28:

```
Ile Glu Thr Arg His Ser Glu Ile Ile Lys Leu Glu Asn Ser Ile Arg
1               5                  10                  15
Glu Leu His Asp Met Phe Met Asp
            20
```

(2) INFORMATION FOR SEQ ID NO:29:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: linear -continued (ii) MOLECULE TYPE: peptide (xi) SEQUENCE DESCRIPTION: SEQ ID NO:29:

```
Ala Leu Ser Glu Ile Glu Thr Arg His Ser Glu Ile Ile Lys Leu Glu
1               5                   10                  15

Asn Ser Ile Arg Glu Leu His Asp Met Phe Met Asp
            20                  25
```

PEPTIDE INHIBITORS OF NEUROTRANSMITTER SECRETION BY NEURONAL CELLS

RELATED UNITED STATES PATENT APPLICATIONS

This application is a continuation-in-part of U.S. Provisional Application Ser. No. 60/013,599, filed on Mar. 18, 1996.

BACKGROUND OF THE INVENTION

1. Field of the Invention

The invention is directed to peptides which inhibit the release of neurotransmitters from synaptic vesicles. More specifically, the invention provides peptides which mimic the inhibitory effect of *Clostridium botulinum* and *tetani* neurotoxins on the neurosecretory process.

2. History of the Invention

Botulinum neurotoxins (including the A, B, C, D, E, F and G serotypes produced by the anaerobic bacterium *Clostridium botulinum*; collectively, "BoTx"), and Tetanus neurotoxin (produced by the anaerobic bacterium *Clostridium tetani*; "TeTx") cause temporary paralysis of muscle by blocking the presynaptic release of acetylcholine at the neuromuscular junction. A purified form of BoTxA is used clinically to alleviate chronic muscle spasm (such as occurs in dystonias, cerebal palsy and muscular dystrophy) through injection into the overactive muscle where it produces a dose-related weakness (for reviews of current therapeutical uses of botulinum toxins, see Jankovic, *Curr. Op. Neurol.* 7358–366 (1994); Borodic, et al., *Drug Safety* 3:145–152 (1994); and, Hughes, *Drugs* 48:888–893 (1994)). BoTxA is also becoming a popular, albeit unapproved, agent for use in minimizing facial wrinkles for those with no interest in aging gracefully (see, e.g., Tanouye, "A Few Wrinkles Still Remain in Quest for Youthful Skin", *The Wall Street Journal* (Feb. 10, 1997)).

Despite their clinical significance, obstacles to widespread use of Clostridium neurotoxins exist, including instability of the toxins at room temperature, immunogenicity and toxicity-related limitations on their purification and storage.

SUMMARY OF THE INVENTION

The invention provides peptides which mimic certain desirable characteristics of Clostridium neurotoxins while avoiding many of the obstacles to their clinical use. In particular, like Clostridium neurotoxins, the peptides of the invention (excitation-secretion uncoupling peptides, or "ESUPs") inhibit secretion of neurotransmitters (e.g., acetylcholine) from neuronal vesicles into the neuromuscular junction, thereby lessening muscular spasticity. However, unlike Clostridium neurotoxins, ESUPs do not suffer from the immunogenicity, toxicity and limited availability of their bacterial counterparts.

More specifically, ESUPs display antispastic activity, high specificity and low toxicity in vivo, with therapeutic effects which last for periods ranging from several days to weeks. Thus, therapeutic use of the ESUPs of the invention in lieu of Clostridium neurotoxins for all clinical applications to which such toxins are suited both reduces the incidence of unwanted side effects and allows therapy to be rapidly discontinued if unwanted side effects appear.

Further, due to their lower immunogenicity, administration of ESUPs in lieu of natural toxin reduces the onset of resistance, skin reactions and flu-like symptoms that occasionally accompany BoTx therapy.

ESUPs are also relatively straightforward to produce (by, for example, solid-phase peptide synthesis) as compared to the presently available manufacturing techniques which are used to prepare BoTx compounds for therapeutic use (see, e.g., Hambleton, *J. Neurol.,* 239:16–20, 1992). Further, the ESUP manufacturing process does not require the stringent containment conditions involved in toxin production.

The ESUPs of the invention comprise synthetic and purified peptide fragments which correspond in primary structure to peptides which serve as binding domains for the assembly of a ternary protein complex ("docking complex") which is believed to be critical to neuronal vesicle docking with the cellular plasma membrane prior to neurotransmitter secretion. Preferably, the primary sequence of the ESUPs of the invention also includes amino acids which are identical in sequence to the peptide products of BoTx and TeTx proteolytic cleavage of their respective natural substrates in neuronal cells, or fragments thereof ("proteolytic products"). For optimal activity, ESUPs of the invention have a minimum length of about 20 amino acids and a maximal length of about 28 amino acids.

Thus, in one embodiment of the invention, the ESUPs correspond in primary structure to binding domains in the docking complex, most preferably the region of such binding domains which are involved in the formation of a coiled-coil structure in the native docking complex proteins.

In another embodiment of the invention, the ESUPs further comprise proteolytic products of the cleavage of synaptosomal associated protein (25 kDa; "SNAP-25") by BoTx serotypes A, E and C.

In an alternative embodiment of the invention, the ESUPs further comprise proteolytic products of the cleavage of vesicle-associated membrane protein ("VAMP-2", also known in the art as "synpaptobrevin") by BoTx serotypes B, D, F and G, as well as by TeTx.

In another alternative embodiment of the invention, the ESUPs are mixed with peptides which comprise proteolytic products of the cleavage of syntaxin by BoTx serotype C1.

For use in clinical applications, pharmaceutical compositions of the ESUPs of the invention are disclosed. ESUPs may also be used as pharmaceutical carriers as part of fusion proteins to deliver substances of interest into neural cells in a targeted manner.

DETAILED DESCRIPTION OF THE DRAWINGS

FIG. 3 is a schematic identifying the relationship of SNAP-25 derived ESUPs to the BoTx A and BoTxE cleavage sites in, and proteolytic products of cleavage from, human SNAP-25. Full-length SNAP-25 (SEQ.ID.NO. 1) is diagramed at the top of the FIGURE, where the amino acids corresponding to the VAMP-2 binding domain are shown in bold. The BoTx A and BoTxE cleavage sites are indicated by vertical arrows in the top diagram. The VAMP-2 binding domain is diagramed in an exploded view in the center of the FIGURE, where the proteolytic products of SNAP-25 neurotoxin cleavage are shown to the right of the diagonal arrow connecting the BoTx cleavage site in the top diagram to the center diagram. The series of bars at the bottom of the FIGURE represent various ESUPs. The composition of each ESUP corresponds to a fragment of matching length and position in the VAMP-2 binding domain shown in the center of the FIGURE. Each ESUP is identified by a letter identifying the cleaving BoTx serotype (A or E), an Arabic numeral corresponding to the number of amino acids which make up the ESUP and the letter "h", meaning that the ESUP is of human origin.

Figure 4:
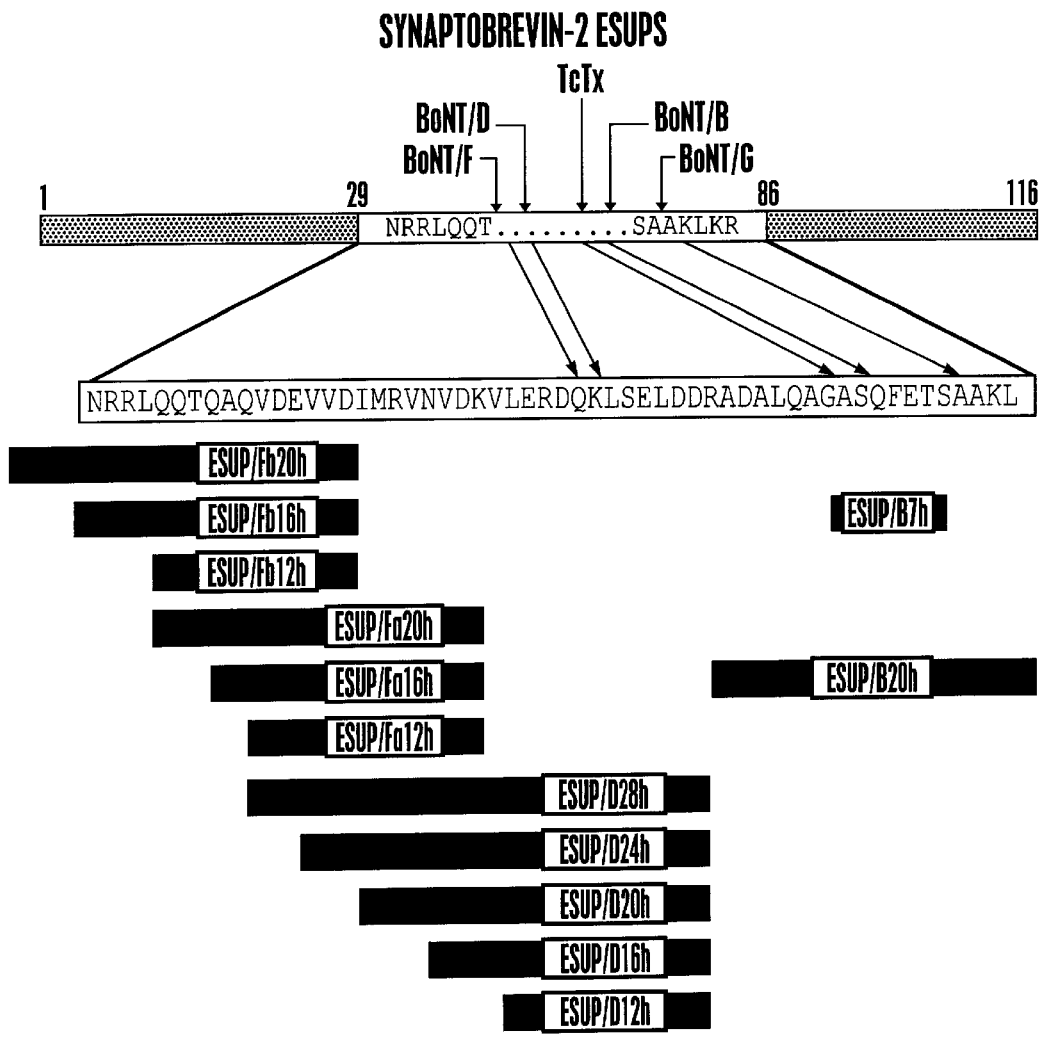

FIG. 4 is a schematic identifying the relationship of exemplary ESUPs to the BoTx A and BoTxE cleavage sites in, and proteolytic products of cleavage from, human synaptobrevin (VAMP-2). Full-length VAMP-2 (SEQ.ID.NO. 2) is diagramed at the top of the FIGURE, where the amino acids corresponding to the SNAP-25/syntaxin binding domain are shown in bold. The BoTx B, D, F and BoTxG cleavage sites, as well as the TeTx cleavage site, are indicated by vertical arrows in the top diagram. The SNAP-25/syntaxin binding domain is diagramed in exploded view in the center of the FIGURE, where the proteolytic products of VAMP-2 neurotoxin cleavage are shown to the right of the diagonal arrow connecting the BoTx cleavage sites in the top diagram to the center diagram. The series of bars at the bottom of the FIGURE represent various ESUPs. The composition of each ESUP corresponds to a fragment of matching length and position in the SNAP-25/syntaxin binding domain diagramed in the center of the FIGURE. Each ESUP is identified by a letter identifying the cleaving BoTx serotype (B, D, F or G), an Arabic numeral corresponding to the number of amino acids which make up the ESUP and the letter "h", meaning that the ESUP is of human origin.

FIG. 5 is a schematic identifying the relationship of exemplary ESUPs to the BoTxC1 cleavage sites in, and proteolytic products of cleavage from, rat syntaxin. Full-length syntaxin (SEQ.ID.NO. 3) is diagramed at the top of the FIGURE, where the amino acids corresponding to the SNAP-25/VAMP-2 binding domain are shown in bold. The BoTx C1 cleavage site are indicated by vertical arrows in the top diagram. The SNAP-25/VAMP-2 binding domain is diagramed in exploded view in the center of the FIGURE, where the proteolytic product of syntaxin neurotoxin cleavage are shown to the right of the diagonal arrow connecting the BoTx cleavage sites in the top diagram to the center diagram. The series of bars at the bottom of the FIGURE represent various ESUPs. The composition of each ESUP corresponds to a fragment of matching length and position in the SNAP-25/VAMP-2 binding domain diagramed in the center of the FIGURE. Each ESUP is identified by a letter identifying the cleaving BoTx serotype (B, D, F or G), an Arabic numeral corresponding to the number of amino acids which make up the ESUP and the letter "h", meaning that the ESUP is of human origin.

Figure 6A:
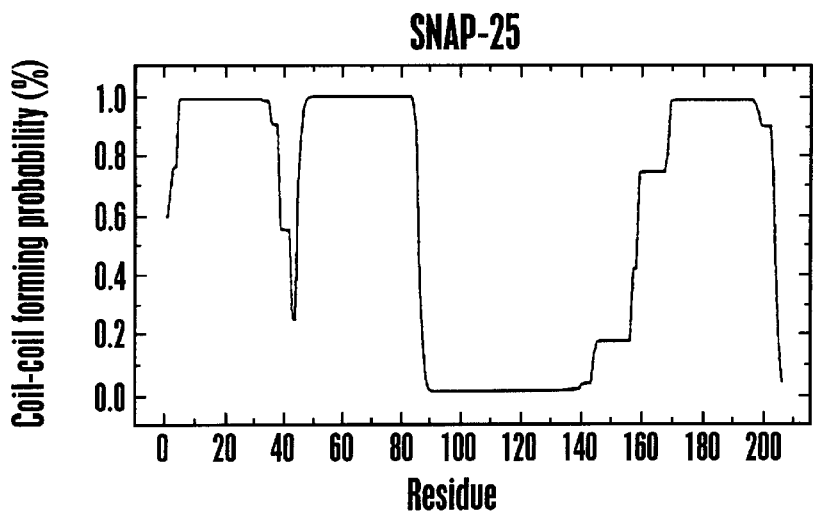
Figure 6B:
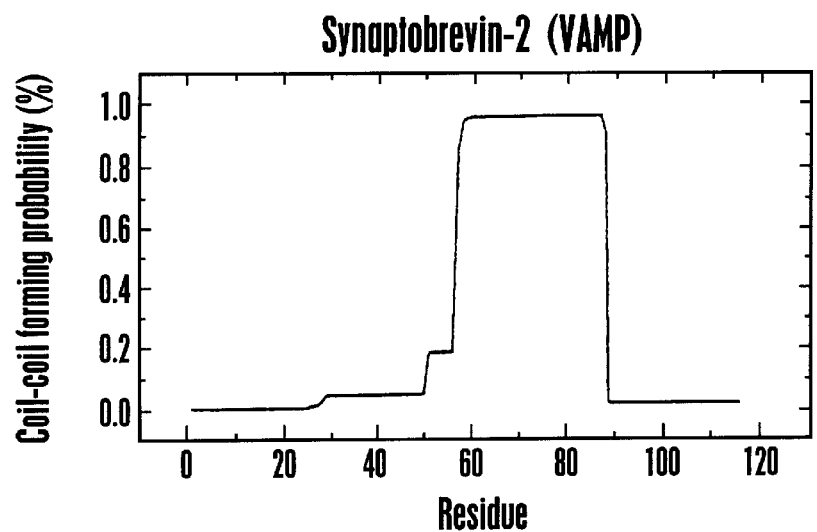
Figure 6C:
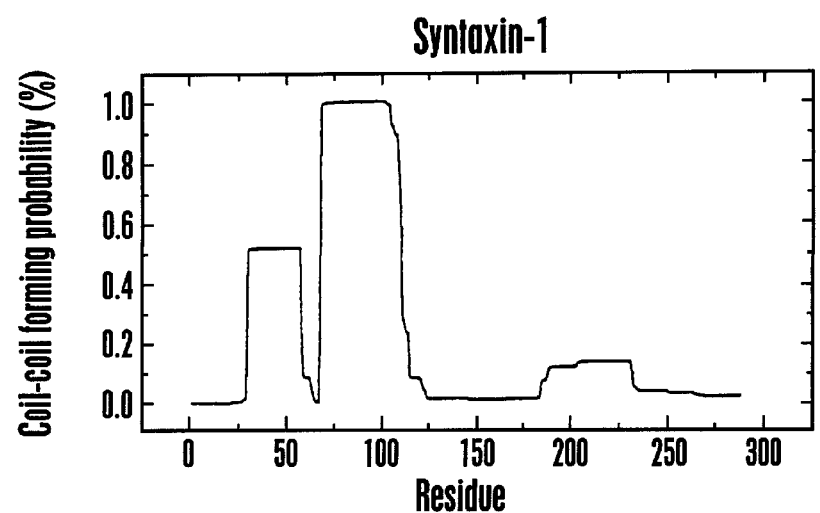

FIGS. 6A, 6B and 6C are graphs depicting coiled-coil sequence predictions in a 28 amino acid (residue) window for, respectively, SNAP-25, VAMP-2 and syntaxin.

Figure 7A:
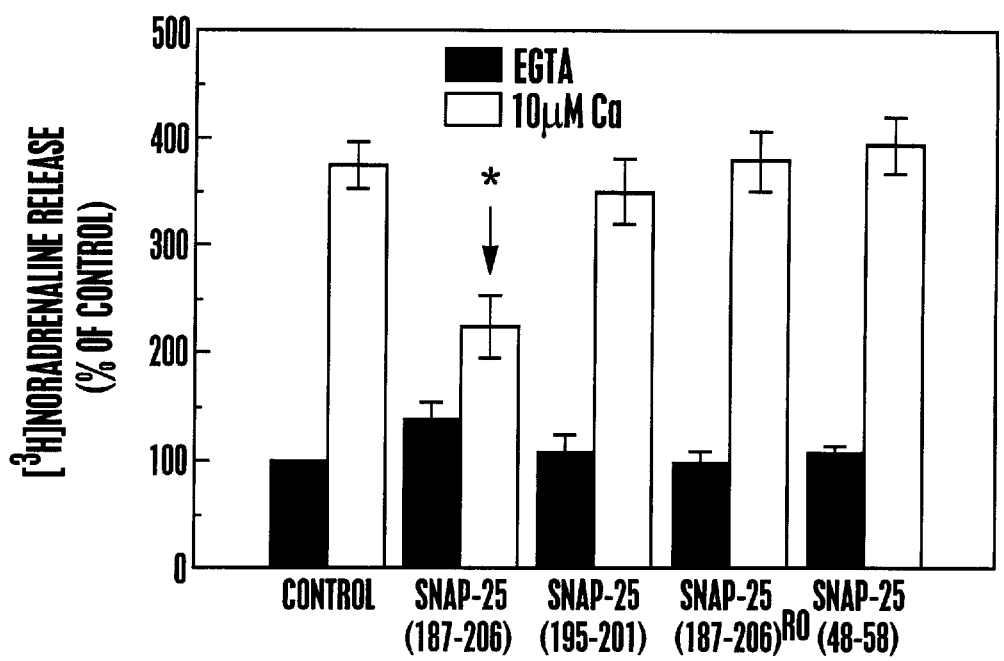
Figure 7B:
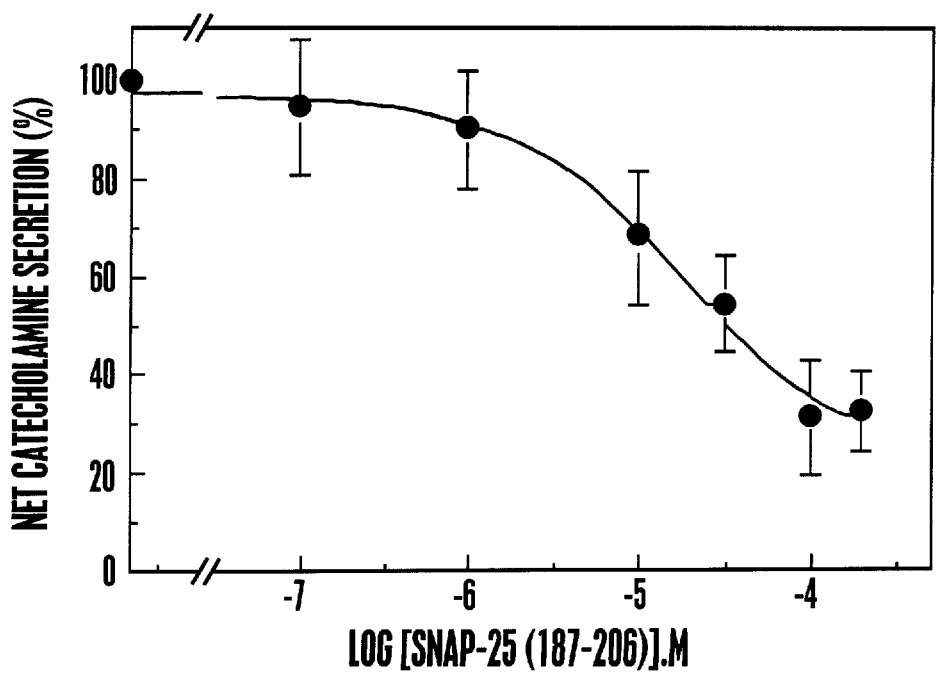

FIGS. 7A, and 7B are graphs depicting, respectively, inhibition of $Ca_{2+}$ dependent synaptic exocytosis by various SNAP-25 peptides at 100 $\mu$M concentration and by ESUP/A20h at varying concentrations. Data represent mean results of 4 experiments. The control is no peptide (P<0.01). Each ESUP is identified by a letter identifying the cleaving BoTx serotype (A or E), an Arabic numeral corresponding to the number of amino acids which make up the ESUP and the letter "h", meaning that the ESUP is of human origin. ESUP A20h corresponds to the entire 20-mer C terminus of SNAP-25.

DETAILED DESCRIPTION OF THE INVENTION

A. Definitions

The following definitions are useful in understanding many of the abbreviations and terms of art used in this disclosure.

1. "ESUP" refers to excitation-secretion uncoupling peptide. Functionally, an ESUP of the invention blocks binding between peptides involved in docking of vesicles to the plasma membranes of neural cells prior to vesicle exocytosis and neurotransmitter secretion.
2. "SNARE" refers to the soluble NSF attachment protein receptor model for exocytosis in neural and endocrine cells.
3. "SNAP" refers to soluble NSF attachment protein. αSNAP is a SNAP protein isoform.
4. "SNAP-25" refers to synaptosomal associated protein (25 kDa weight). SNAP-25 is not related to SNAP.
5. "VAMP-2" refers to vesicle associated membrane protein, also known as synaptobrevin.
6. "Corresponds to", and "corresponds in sequence to", as used in reference to an ESUP, refer to the portion of SNAP-25, VAMP-2 or syntaxin which is identical in amino acid sequence to the ESUP in question.
7. "NSF" refers to N-ethylmaleimide-sensitive fusion protein. NSF is an ATPhase.
8. "Exocytotic cascade" refers to the $Ca^{2+}$ regulated process for exocytosis of vesicles associated with the release of neurotransmitters from neural cells and hormones from endocrine cells.
9. "Target substrate" refers to the substrate for ESUP binding. Depending on which protein the ESUP primary structure corresponds to, the target substrate will be VAMP-2, SNAP-25 or syntaxin.
10. "Docking complex" refers to a ternary protein complex which consists of VAMP-2, SNAP-25 and syntaxin that is believed to facilitate neuronal vesicle docking with the cellular plasma membrane prior to exocytosis.
11. "Docking complex protein" refers to VAMP-2, SNAP-25 and/or syntaxin.
12. "Substrate binding domain" refers to the regions of VAMP-2, SNAP-25 and syntaxin which bind one another to form the docking complex.

B. Formation of the Docking Complex which is Inhibited by the ESUPs of the Invention The SNARE model describes the final steps of the exocytotic cascade as being comprised of three distinct stages: vesicle docking, vesicle priming and vesicle fusion (to the plasma membrane). Docking is associated with the formation of a protein complex between VAMP-2 (on the vesicle membrane), SNAP-25 and syntaxin (both plasma membrane proteins). The resulting complex serves as a receptor for SNAP proteins and recruits NSF. ATP hydrolysis by bound NSF energizes the vesicles into a primed state. Once primed, the vesicles can fuse with the plasma membrane and release their contents (such as acetylcholine) in response to the appropriate $Ca^{2+}$ signal.

Figure 1:
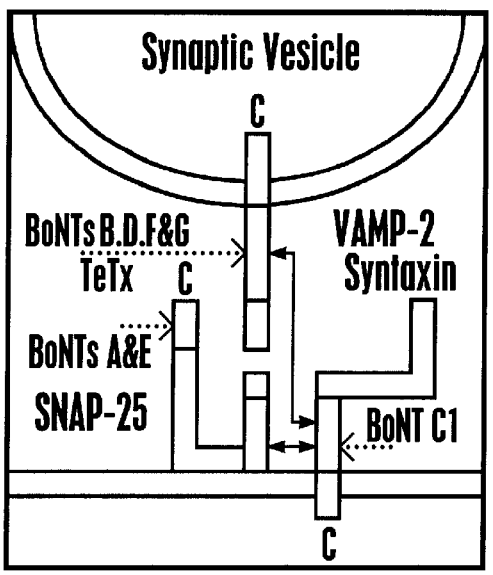
FIG. 1 is a schematic drawing depicting the location of, and interactions between, SNAP-25, VAMP-2 (synaptobrevin) and syntaxin, as well as the regions of each synaptic vesicle fusion core complex protein cleaved by Clostridium neurotoxins BoTx A, B, C, D, E, F and G, as well as TeTx.

SNAP-25, VAMP-2 and syntaxin bind together very tightly with a equimolar stoichiometry, forming a stable ternary complex (Hayashi, et al., *EMBO J.* 13:5051–5061 (1994) and FIG. 1). VAMP-2 and syntaxin initially bind at low affinity (i.e., the apparent $K_d$ is in the micromolar range), which affinity increases substantially in the presence of SNAP-25. Once formed, the docking complex bridges the synaptic vesicle to the plasma membrane, and serves as binding site for α-SNAP and NSF (McMahon, et al., *J. Biol. Chem.* 270:2213–2217 (1995)), which mediate the final fusion step of vesicle exocytosis. The schematic in FIG. 1 summarizes the currently available information about the protein binding interactions which lead to the formation of the docking complex and vesicle exocytosis.

The amino acid sequences of, respectively, the full length SNAP-25, VAMP-2 and syntaxin proteins are set forth in SEQ.ID.Nos. 1–3. The substrate binding domain regions of VAMP, SNAP-25 and syntaxin are diagrammed in FIGS. 3–5 and are:
For human SNAP-25
170-EIDTQNRQIDRIMEKADSNKTRIDEANQRATK MLGSG-206
(SEQ.ID.NO. 4)
For human VAMP-2
29-NRRLQQTQAQVDEVVDIMRVNVDKVLERDQKLS ELDDRADALQAGASQFETSAAKLR-86
(SEQ.ID.NO. 5)
For rat syntaxin (at present, the human sequence is unknown, but is expected to share a high degree of homology with the rat sequence):
199-HSEIIKLENSIRELHDMFMD-218
(SEQ.ID.NO. 6)

Any interference which disrupts either the assembly of the docking complex can potentially uncouple the excitatory event (membrane depolarization and increase in permeability to $Ca^{2+}$) from downstream events which result in neurotransmitter release (synaptic vesicle fusion with the plasma membrane). To that end, the ESUPs of the invention inhibit docking complex formation by a mechanism which is believed to mimic the inhibitory activity of Clostridium neurotoxins on binding between VAMP-2, SNAP-25 and syntaxin.

C. ESUP Structure and Presumed Mechanism of Action

In vivo, BoTx serotypes A and E cleave SNAP-25 (see, e.g., Binz, et al., *J. Biol. Chem.* 269:1617–1620(1994); Schiavo, et al., *FEBS Lett.* 33599–103 (1993); Schiavo, et al., *J. Biol. Chem.* 268:23784–23787 (1993); and, Blasi, et al., *Nature* 365:160–163 (1993)), while BoTx C1 acts on syntaxin (see, e.g., Schiavo, et al., *J. Biol. Chem.* 270:10556–10570 (1995)) and BoTx B, D, F and G specifically cleave VAMP-2 (see e.g., Schiavo, et al., *J. Biol. Chem.* 268:23784–23787 (1993); Yamasaki, et al., *Biochem. Biophys. Res. Comm.* 200:829–835 (1994); and, Yamasaki, et al., *J. Biol. Chem.* 269:12764–12772 (1994)).

In vivo, TeTx cleaves VAMP-2 and shares substantially the same mode of action of BoTx (i.e., TeTx acts as an anticholinergic, presynaptic neurotoxin), as well as a substantial degree of sequence homology with BoTx A and E (DasGupta, et al., *Biochemie,* 71:1193–1200, 1989). Thus, together with their substrate binding domains, the regions of SNAP-25, VAMP-2 and syntaxin cleaved by the BoTx serotypes and by TeTx are of interest in the invention (see FIGS. 3–5).

While the invention is not limited by any particular theory concerning the mechanism of action for ESUPs, the presumed mechanism of action for ESUP inhibition of neurotransmitter release is as follows. ESUPs correspond in whole or in part to the substrate binding domains whose interaction leads to the formation of the docking complex. By selectively interfering with binding between the docking complex proteins, it is possible to prevent vesicle docking and, as a consequence, to inhibit neurotransmitter secretion.

In the invention, it is believed that such binding interference is provided by ESUPs through competition for binding between docking complex proteins. ESUPs may also serve as barriers to the conformational changes needed to render the docking complex sufficiently stable to serve as a vesicle receptor.

The ESUPs of the invention share common structural characteristics. Each consists of at least about 20 amino acids which correspond in sequence to all or a portion of the substrate binding domains of, respectively, VAMP for SNAP-25 and syntaxin; SNAP-25 for VAMP and syntaxin; and, syntaxin for VAMP and SNAP-25 (see, FIGS. 3–5 and SEQ.ID.Nos. 4–6). Preferably, ESUPs derived from VAMP-2 or SNAP-25 further correspond in sequence to all or a part of the proteolytic product of docking complex protein cleavage by at least one neurotoxin (BoTx or TeTx), and may also include the cleavage site(s).

For ESUPs derived from syntaxin, the BoTxC 1 cleavage site is between residues 253 and 254, 35 residues upstream from the carboxyl end of the syntaxin substrate binding domain (199–218). Thus, inclusion in an ESUP of the cleavage site, proteolytic product of BoTxC1 cleavage and the residues which bridge these regions to the binding domain would result in an peptide having a length well in excess of 28 amino acids. Although such a peptide would be expected to have the inhibitory activity provided by ESUPs of the invention, its length would diminish the usefulness of the peptide for in vivo applications. To avoid this difficulty, syntaxin derived ESUPs may be comprised of binding domain residues only (see, e.g., FIG. 5) and may optionally be fused to, or administered with, peptides which consist of portions of the BoTxC1 proteolytic product and/or cleavage site.

In addition, although docking complex proteins have regions which are conserved to some extent, the most preferred ESUPs will correspond in sequence to regions of human docking complex proteins or, where the human sequence is not presently known (i.e., for syntaxin), will correspond to a known mammalian sequence (e.g., for the rat or bovine protein).

Surprisingly, certain ESUPs exhibit strong inhibitory activity (50% or greater inhibition of neurotransmitter release as compared to a control, described further infra) at relatively low concentrations (10 μM or less). Such ESUPs have the ability to form a coiled-coil structure and therefore tend to be greater than about 20 amino acids in length. Advantageously, however, the ESUPs need be no longer than about 28 amino acids in length to possess strong inhibitory activity. Thus, ESUPs of the invention are particularly well suited to in vivo use, where smaller peptides are greatly preferred.

More particularly, coiled-coil structures are believed to assist ESUPs in interacting with docking complex proteins in vivo. It has been suggested that docking complex proteins themselves contain heptads which are characteristic of α-helices that form coiled-coil structures. Coiled-coils consist of two or more right handed a-helices wrapped around each other into a compact structure with a left-handed superhelical twist.

The commercially available computer software program COILS (whose use is described in Lupas, et al., *Science* 252:1162–1164 (1991), which is incorporated herein for purposes of reference) is useful to identify heptad repeats inside the substrate binding domains of docking complex proteins. A protocol to identify potential coiled-coil regions within SNAP-25, VAMP-2 and syntaxin is also described in Example III. As shown in FIGS. 6A–C, certain regions of SNAP-25, VAMP-2 and syntaxin exhibit a high probability of forming coiled-coils (particularly the C terminus of SNAP-25). For example, in SNAP-25, the consensus sequence for the complete binding domain is between residues 167 and 206 (167-MGNEIDTQNRQIDRIMEKA DSNKTRIDEANQRATKMLGSG-206; SEQ.ID.NO.4); and consists of CCHHHHHHHHHHHHHHHHHHCCCCH HHHHHHHHHHHHHHHCCC (where H: α-helix, T: Turn and C: Random Coil (determined by the SOPM method; Geourjon, et al., *Protein Engineering* 7:157–164 (1994)). Within the SNAP-25 binding domain, there are two predicted α-helix forming regions (at residues 169–185 and at residues 190–203).

Substantially all of the amino acids which comprise the ESUPs of the invention correspond to portions of the substrate binding domain regions of SNAP-25, VAMP-2 or syntaxin, including at least one coiled-coil structure. Preferably, the ESUPs also include binding domain regions which correspond to the proteolytic product of BoTx/TeTx cleavage of SNAP-25 or VAMP-2. In the latter embodiment, where the proteolytic product of cleavage is less than 28 amino acids in total length, the ESUP includes additional residues corresponding to contiguous binding domain residues upstream of the cleavage site or downstream of the proteolytic product terminus. For ESUPS which include less than all of the substrate binding domain, it is preferred that ESUPs which correspond in sequence to the substrate binding domain of SNAP-25 include residues from the C terminus of SNAP-25 (residues 187–206).

In general, inclusion of additional cleavage sites and proteolytic product residues in addition to coiled-coil region substrate binding domain residues can be expected to enhance activity. However, while peptides encompassing all of these regions are within the scope of the invention, relatively short peptides (e.g., of about 28 amino acids or less) are preferred for use as peptide drugs in vivo.

ESUPs which correspond in sequence to portions of the substrate binding domain region of SNAP-25 tend have strong inhibitory activity and are therefore preferred ESUPs of the invention. SNAP-25 is interesting in that the cleavage sites of both BoTx A and BoTx E are in the region of SNAP-25 that interacts with VAMP-2. These cleavage sites are distinctive (e.g., botulinum toxins A and E sever only short sequences from the C-terminal region of SNAP-25 whereas the other toxins release large portions of their target proteins). The C-terminal region of SNAP-25 is critical for the generation of a stable docking complex, and its cleavage markedly inhibits the binding of SNAP-25 to VAMP-2.

Exemplary SNAP-25 ESUPs include

1. ESUP/E20h.
   a. Primary Structure: 170-EIDTQNRQIDRI MEKADSNK-189 (SEQ.ID.NO. 7; includes the site for BoTxE cleavage, all but one residue of a coiled-coil region of SNAP-25 and 9 amino acids of the 16 amino acid proteolytic product of BoTxE cleavage. All residues correspond to substrate binding domain residues.)
   b. Inhibitory Activity: 50% at 1.8 μM, as measured in the bovine chromaffin inhibition assay described in Example II.
2. ESUP/E26h
   a. Primary Structure: 181-IMEKADSNKTRIDEAN QRATKMLGSG-206 (SEQ.ID.NO. 8; includes the site for BoTxE cleavage, all of the proteolytic product of BoTxE cleavage, the site for BoTxA cleavage, all of the proteolytic product of BoTxA cleavage and all of one coiled-coil region of SNAP-25. All residues correspond to substrate binding domain residues.)
   b. Inhibitory Activity: 50% at 0.25 μM, as measured in the bovine chromaffin inhibition assay described in Example II.
3. ESUP/A20h
   a. Primary Structure: 187-SNKTRIDEAN QRATKMLGSG-206 (SEQ.ID.NO. 9; includes the site for BoTxA cleavage, all of the proteolytic product of BoTxA cleavage, 11 of the 16 amino acids of the proteolytic product of BoTxE cleavage and all of one coiled-coil region of SNAP-25. All residues correspond to substrate binding domain residues.)
   b. Inhibitory Activity:
      i. 50% at 12 μM; 65% at 100 μM, as measured in the bovine chromaffin inhibition assay described in Example II.
      ii. 47% at 2 μM; 87% at 20 μM, as measured in the mouse neuron inhibition assay described in, for example, Mehta, et al., *Proc. Natl. Acad. Sci. USA*, 93:10471–10476, 1996 (incorporated herein for purposes of reference).

Those of ordinary skill in the art will recognize that other ESUPs having the inhibitory activity desired in the invention can be readily identified in view of the criteria set forth above and constructed using synthesis and purification techniques which are conventional in the art. Certain such ESUPs are diagramed in FIGS. 3–5 and are identified in SEQ.ID.Nos. 12–29.

D. Synthesis and Purification of ESUPs

ESUPs can be readily synthesized by conventional techniques, such as the solid phase synthesis techniques as described in Gutierrez, et al., *FEBS Letters*, 372:39–43 (1995), the disclosure of which is incorporated herein by this reference to illustrate knowledge in the art concerning techniques for the production of synthetic peptides.

Briefly, commonly used methods such as t-BOC or FMOC protection of alpha-amino groups are suitable for use in synthesizing ESUPs of the invention. Both methods involve stepwise syntheses whereby a single amino acid is added at each step starting from the C terminus of the peptide (see, Coligan, et al., *Current Protocols in Immunology*, Wiley Interscience, 1991, Unit 9). Peptides of the invention can also be synthesized by various well known solid phase peptide synthesis methods, such as those described by Merrifield (*J. Am. Chem. Soc.*, 85:2149, 1962), and Stewart and Young (*Solid Phase Peptides Synthesis*, Freeman, San Francisco, 1969, pp 27–62), using a copoly (styrene-divinylbenzene) containing 0.1 –1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on a "SEPHADEX G-15" or "SEPHAROSE" affinity column. Lyophilization of appropriate fractions of the column will yield the homogeneous peptide or peptide derivatives, which can then be characterized by such standard techniques as amino acid analysis, thin layer chromatography, high performance liquid chromatography (HPLC), ultraviolet absorption spectroscopy, molar rotation, solubility, and quantitated by the solid phase Edman degradation.

The synthesis objective is to produce peptides whose charge distribution is similar to that in the native sequence. The selection of resins and post-synthesis treatments for each peptide will therefore be optimized for this result. In particular, resins that yield a free carboxy group are useful to generate peptides representing the C-terminal of a protein. Subsequently, the N-terminal will be acetylated. Resins that yield an aminated C-terminal are useful to generate internal peptides and peptides representing the N-terminal region. For generation of internal sequence peptides, the N-terminal is acetylated, whereas for generation of N-terminus peptides, the N-terminal is free.

In order to increase the bioavailability of the peptides, the sequences corresponding to the most active ESUP peptides are synthesized using standard Fmoc or t-Boc chemistries but with amino acid derivatives in D-conformation. Alternatively, sequences with reduced peptide bonds in positions susceptible to proteolysis may be synthesized according to, for example, Meyer et al., *J. Med. Chem.*, 38:3462–3468 (1995) (incorporated herein for reference). Briefly, such peptides are synthesized using a Fmoc/tert-butyl strategy, and the Y($CH_2NH$) bonds, or reduced bonds, are introduced via reductive alkylation of the N-terminal amino group of the growing peptide with a Fmoc-Na-protected amino aldehyde.

Substitution of amino acids (i.e., to vary from the identity or order of the corresponding residues in the relevant docking complex protein) within ESUPs is not desirable. As shown in FIG. 7A, randomization of the amino acids in an otherwise inhibitory ESUP results in loss of inhibitory activity. Thus, while minor substitutions or deletions may not have a deleterious effect on ESUP activity, avoidance of such modifications is preferred.

To increase the efficacy of selected peptides so they can exert their physiological effect for longer periods of time, the following refinements to ESUPs of the invention may be made using techniques which those of ordinary skill in the art will be familiar with or can readily ascertain.

The acetylation of N-terminal a-amino group or the choice of N-terminal amino acid can dramatically improve the α-helical stability (Chakrabartty, et al., *Proc. Natl. Acad. Sci. USA* 90:11332–11336 (1993); Jarvis, et al., *J. Biol. Chem.* 270:1323–1331 (1995)) and biological activity of a peptide (Dooley, et al., *Science* 266:2019–2022 (1994)). N-terminal acetylation has also been described as a factor which contributes to the stabilization of coiled-coil forming peptides (Greenfield, et al., *Protein Science* 3:402–410 (1994)) and to increase resistance to proteolytic degradation by exopeptidases (Abiko, et al., *Chem. Pharm. Bull.* 39:752–756 (1991)). ESUPs of the invention may therefore be modified to have enhanced activity and stability by acetylation of their N-termini.

D-isomers of the ESUPs of the invention are also desirable for their resistance to proteolytic degradation in vivo. It is well recognized that L-bond peptides are susceptible to proteolytic degradation, restricting their application as drugs. However, this obstacle has been successfully bypassed in some cases by synthesizing analogues which contain D-bond amino acids or non-natural amino acids. The addition of a single D-amino acid at the C-terminal position is enough to enhance the resistance to proteolytic degradation by exopeptidases, without significantly altering the secondary structure of the peptide (Abiko, supra). Resistance to endopeptidases can be achieved by including individual non-cleavable non-peptidic bonds in points in the peptide sequence that are specially sensitive to enzymatic degradation (Meyer, et al., *J. Med. Chem.* 38:3462–3468 (1995); Guichard, et al., *Peptide Research* 7:308–321 (1994)). Reverse amide bonds Y[NHCO], reduced amide bonds Y[$CH_2NH$] or retro-reduced bonds Y[$NHCH_2$] can be used as surrogates of the amide link [CONH] in ESUPs of the invention. Reduced amide links are preferred, since they result only in minor destabilization of a-helices (Dauber-Osguthorpe, et al., *Int. J. Pep. Prot. Res.* 38:357–377 (1991)).

Alternatively, ESUPs can be synthesized in all-D-conformations. All-D-peptides can be equally active as the original all-L-peptides (Merrifield, et al., *Ciba Foundation Symposium* 186:5–20 (1994); Wade, et al., *Proc. Natl. Acad. Sci. USA* 87:4761–4765 (1990)), capable of successfully resisting enzymatic degradation and less immunogenic than their all-L-analogues (King, et al., *J. Immunol.* 153:1124–1131 (1994)).

Interestingly, the ESUPs of the invention can be used in fusion proteins for targeted delivery other substances of interest into neural cells. In this respect, the ESUP may be used in lieu of a Clostridium neurotoxin (e.g., where used for delivery of Substance P into brain tumor cells to cause apoptosis; see, Fisher, et al., *Proc. Nat'l. Sci. Acad. USA*, 93:7341–7345 (1996), the disclosure of which is incorporated herein for reference) or in lieu of other carriers for delivery of the substance of interest. Those of ordinary skill in the art will be familiar with, or can readily ascertain, suitable techniques for binding an ESUP to a substance of interest (i.e., a drug) for use in this embodiment of the invention.

To confirm the intracellular distribution of ESUPs in vivo, each can be attached to a label which is detectable in vivo. For this purpose, the concentration of detectably labeled ESUP which is administered should be sufficient such that the binding to the target protein is detectable compared to the background. Further, it is desirable that the detectably labeled ESUP be rapidly cleared from the circulatory system in order to give the best target-to-background signal ratio.

For in vivo imaging, the type of detection instrument available is a major factor in selecting a given detectable label; e.g., a radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized.

Ideally, a radioisotope used for in vivo imaging will lack a particle emission, but produce a large number of photons in the 140–250 keV range, which may be readily detected by conventional gamma cameras. Typical examples of metallic ions which can be bound to the ESUPs of the invention are $^{111}$In, $^{97}$Ru, $^{67}$Ga, $^{68}$Ga, $^{72}$As, $^{89}$Zr, $^{90}$Y, and $^{201}$Tl.

ESUPs can also be labeled with a paramagnetic isotope for purposes of in vivo imaging, as in magnetic resonance imaging (MRI) or electron spin resonance (ESR) techniques. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

A representative method for solid-phase synthesis of ESUPs is described in Example I. Those of ordinary skill in the art will, however, recognize that techniques other than those specifically described will also be useful in synthesizing and purifying ESUPs which meet the criteria of the invention.

E. Pharmaceutical ESUP Compositions and Uses

Pharmaceutically useful compositions of ESUPs are prepared by mixing an ESUP of interest with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

Such compositions may be lyophilized for storage and will be reconstituted according to pharmaceutically acceptable means; i.e., suitably prepared and approved for use in the desired application. A sodium chloride free buffer is preferred for use as a reconstituting agent. Inclusion of bovine or human serum albumin (BSA or HSA) in the composition or reconstituting agent has also been reported to assist in recovery of toxin activity after reconstitution from a lyophilized state (see, e.g., published EPO application No. 0 593 176 A2). Whatever its form, the composition product will be placed into sterile containers (e.g., ampules) for storage and transportation. Advantageously, even in reconstituted form, ESUPs can be expected to be stable when stored at room temperature for far longer than natural Clostridium toxins, which lose activity within minutes of reconstitution from the lyophilized state.

Clinically, the ESUPs of the invention will be useful in the same therapies which are or may be practiced with Clostridium neurotoxins. Protocols for administering ESUPs (including dosing schedules and concentrations) will be similar to the clinical regimes for neurotoxin administration, although the lower immunogenicity and high inhibitory activity of ESUPs (particularly those exhibiting strong inhibitory activity as defined herein) will permit lower dosages and fewer applications to be provided, depending on the patient's condition and the medical judgment of the clinician (see, representative dose response curve set forth in FIG. 2). The concentration of an ESUP of the invention in a pharmaceutically acceptable carrier which produces a therapeutic benefit in a host that can also be provided by a Clostridium neurotoxin, but is provided in lieu of a Clostridium neurotoxin, is considered a "therapeutically effective dosage" of the ESUP.

For reference in regard to the clinical use of Clostridium neurotoxins, interested clinicians may wish to consult Jankovic and Hallett, "Therapy with Botulinum Toxin" (M. Dekker, 1994) and Moore, "Handbook of Botulinum Toxin Treatment" (Blackwell Science, 1995), the disclosures of which are incorporated herein for the purpose of illustrating current clinical uses for Clostridium neurotoxins and, by extension, the ESUPs of the invention. As of March, 1997, information concerning clinical uses for Clostridium neurotoxins can also be found on the World Wide Web at URL http://web.bu.edu/npharm/npharm.htm.

F. Assay for ESUP Activity

ESUPs which meet the criteria of the invention can be identified and their activity confirmed in a number of different in vitro assays for detection of neurotransmitter release from neuronal cells. However, because SNAP-25, VAMP-2 and syntaxin are highly but not completely conserved, assays based on a mammalian biological system are preferred.

Thus, the preferred assay to determine ESUP inhibitory activity with respect to neurosecretion is based on detection of catecholamine release from permeabilized bovine chromaffin cells. These cells possess SNAP-25 and the rest of components of the fusion complex and are sensitive to botulinum toxins (Ahnert-Hilger, et al., Neuroscience 53:547–552 (1993); Bartels, et al., J. Biol. Chem. 269:8122–8127 (1994); Bittner, et al., Cel. Mol. Neurobiol. 13:649–664 (1993)).

Catecholamine release is studied in basal conditions and after stimulation with $Ca^{2+}$ to assess if candidate ESUP peptides act specifically at their intended target site and inhibit regulated secretion as compared to a control; i.e., secretion levels from neural cells stimulated with $Ca^{2+}$ with no exposure to an ESUP. For purposes of the invention, possession of the former activity with respect to the control confirms that a candidate peptide is an ESUP of the invention. A detailed protocol for performance of a chromaffin cell inhibition assay is provided in Example II.

The invention having been fully described, examples illustrating its practice are provided below. The examples should not, however, be construed to limit the scope of the invention. Standard abbreviations (e.g., "ml" for milliliters, "h" for hours) are used throughout the examples.

EXAMPLE I

Representative Method for Synthesis of ESUPs

A. Reagents t-Boc and Fmoc amino acids, with standard side chain protecting groups, were obtained from Applied Biosystems (Foster City, Calif.), NovaBio-Chem (La Jolla, Calif.) or Peninsula Laboratories (Belmont, Calif.). Solvents, reagents and resins for peptide synthesis were from Applied Biosystems. All other reagents were of analytical grade from Sigma Chemical.

B. Synthesis

Peptides were synthesized by t-Boc or Fmoc chemistries using an Applied Biosystems 431A automated solid-phase peptide synthesizer, and cleaved as described in King, et al., Int. J. Peptide Protein Res., 36:255, 1990. Cleaved peptides were purified by RP-HPLC on a VydaC™ C-18 semi-preparative column. Samples of crude peptide (10–20 mg) dissolved in 0.1% trifluoroacetic acid were applied to the column and eluted with a linear gradient of 90% acetonitrile in 0.1% trifluoroacetic acid. Eluted peaks were monitored by absorbance measurements at 214 nm, pooled and lyophilized. Peptide purity was assessed by RP-HPLC on a VydaC™ C-18 analytical column.

EXAMPLE II

Inhibitory Effect of ESUPs on Catecholamine Release from Detergent-Permeabilized Chromaffin Cells A. Chromaffin Cell Cultures Chromaffin cells were prepared from bovine adrenal glands by collagenase digestion and further separated from debris and erythrocytes by centrifugation on Percoll gradients (Gomis, et al., Biochem. Pharmacol., 47:225, 1994). Cells were maintained in monolayer cultures at a density of 500,000 cells/cm$^2$ and used between the third and sixth day after plating. All the experiments were performed at 37° C.

B. Determination of Catecholamine Release from Detergent-Permeabilized Chromaffin Cells Secreted [$^3$H]noradrenaline was measured in digitonin-permeabilized cells as described in Gutierrez, et al., Biochem. Biophys Res. Commun. 206:1–7 (1995). Briefly, cells were incubated with [$^3$H]noradrenaline (1 mCi/ml) in DMEM during 4 hours in the presence of 1 mM ascorbic acid. Thereafter, monolayers were washed 4 times with a Krebs/HEPES basal solution: 15 mM HEPES, pH 7.4 with 134 mM NaCl, 4.7 mM KCl, 1.2 mM $KH_2PO_4$, 1.2 mM $MgCl_2$, 2.5 mM $CaCl_2$, 0.56 mM ascorbic acid, and 11 mM glucose.

Cells were permeabilized using 20 mM digitonin in 20 mM Pipes, pH 6.8 with 140 mM monosodium glutamate with 2 mM $MgCl_2$, 2 mM Mg-ATP and 5 mM EGTA for 5 minutes. Permeabilization was carried out in the absence and presence of different peptides. Subsequently, media was discarded and cells were incubated for 10 aditional minutes in digitonin-free medium in presence or absence of additives. Basal or stimulated secretion was measured in media containing 5 mM EGTA or 10 mM $Ca^{2+}$, respectively. Media was collected and released catecholamines and as the total cell content (after lysis in 2% SDS) was quantified by liquid scintillation spectrometry.

C. Results

Synthetic peptides were used in the above-described assay to probe the role of specific protein domains of docking complex proteins in excitation-secretion coupling.

Figure 2:
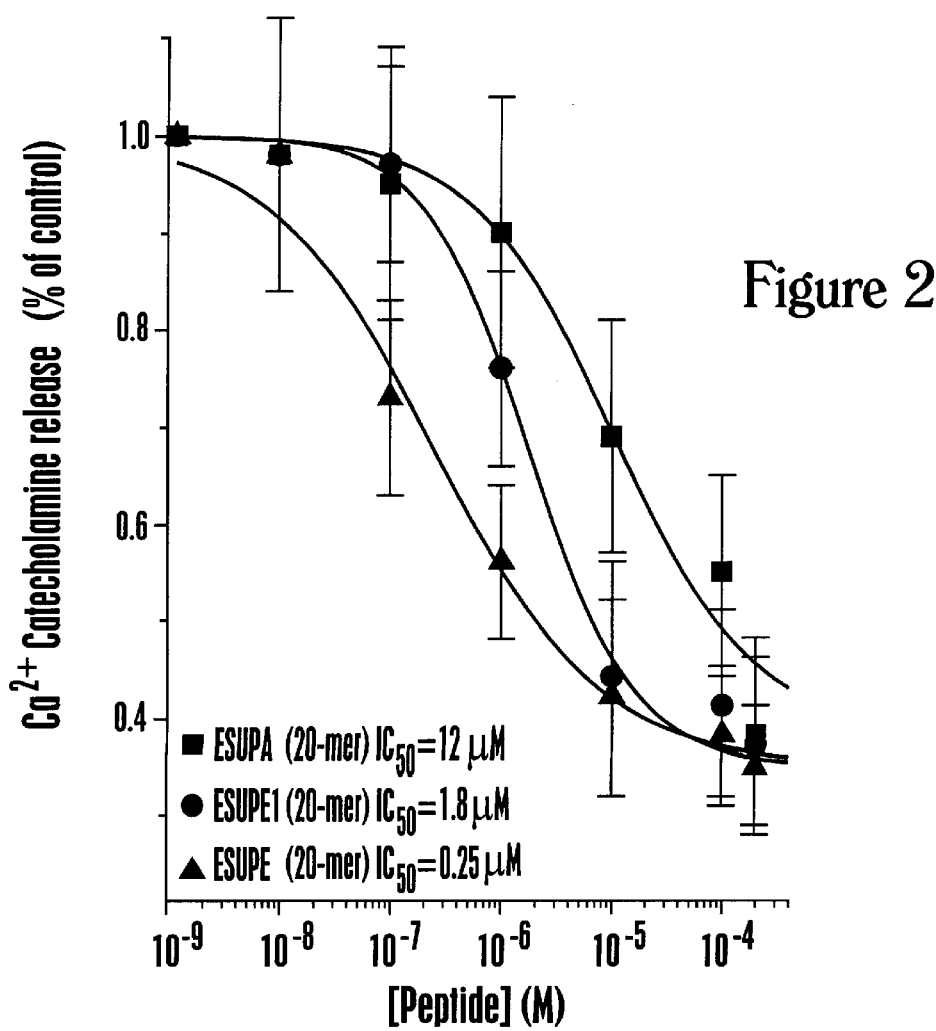
FIG. 2 is a graph depicting a dose response curve for inhibition of $Ca^{2+}$ dependent synaptic exocytosis by SNAP-25 derived ESUPs of 20-mer length or greater which include the proteolytic products of human SNAP-25 cleavage by BoTxE (E26 [▲] and E20 [●]), as well as BoTxA (A20 [■]).

As shown in the dose response curve set forth in FIG. 2, ESUP/E20h (SEQ.ID.NO. 7) reached 50% inhibitory activity at a concentration of 1.8 $\mu$M. Unexpectedly, a relatively minor increase in length to encompass a second cleavage site and proteolytic product (for BoTxA cleavage) dramatically enhanced inhibitory activity; i.e., ESUP/E26h reached 50% inhibitory activity at a concentration of only 0.25 $\mu$M.

A 20-mer peptide encompassing the C-terminal region of SNAP-25 (aa 187–206: SNKTRIDEANQRATKMLGSG; SEQ.ID.NO.9; ESUP/A20h) had lesser, but still significant inhibitory activity, reaching 50% inhibition at 12 $\mu$M (FIG. 2), with a concomittant decline in net catecholamine secretion (FIG. 7B). In contrast, a control peptide, with the same amino acid composition as ESUP/A20h but in random order (FIG. 7A; ESUP/20Ah$^{RD}$: TDSSGREMIKANKQLANGTR, SEQ.ID.NO. 10), had no effect on $Ca^{2+}$ dependent secretion. Shorter peptides were also inactive (FIG. 7A), demonstrating that a minimum peptide length and matched amino acid sequences (corresponding to native configurations) are important for ESUP activity.

A peptide mimicking an N-terminal motif of SNAP-25 outside of its substrate binding region (Rosetto, et al., Nature, 372:415, 1994) (SNAP-25(49–59) (MLDEQGEQLER; SEQ.ID.NO. 11)) did not affect $Ca^{2+}$ -triggered secretion (FIG. 7A).

EXAMPLE III

Method for Secondary Structure Prediction for ESUPs

Coiled-coil predictions are carried out using the commercially available computer program COILS described by Lupas et al. (Lupas, supra; based on Parry, *Biosci. Rep.* 2:1017–1024 (1982), the disclosures of which are incorporated herein by reference). The first selection of putative coiled-coil forming domains is done by comparing the protein sequences to an unweighted MTK matrix (Lupas, supra) using a 28 residues scanning window. A second scanning using a 14 residues window is done in order to pinpoint smaller subdomains. The use of a 28 amino acid scanning window permits a more accurate determination of predicted coiled-coil forming regions, but the spatial resolution is poor. On the other hand, a 14 amino acid scanning window provides better resolution, at the expense of a loss in accuracy in the computation of the probabilities. Predicted coiled-coiled domains are compared with secondary structure predictions obtained using the self-optimized prediction method (SOPM) (Geouijon, et al., *Protein Engineering* 7:157–164 (1994); and, Geourjon, et al., *Comp. Appli. Biosci*., (1995), the disclosures of which are incorporated herein by reference], which provides a consensus secondary structure from five different prediction methods.

In cases where the calculated consensus sequence shows important discrepancies with the coiled-coil predictions, the Q7-JASEP algorithm is also used (Viswanadhan, et al., *Biochemistry* 30:11164–11172 (1991)). This algorithm combines statistical methods which will be known to those of ordinary skill in the art; to wit, the methods of Chou-Fasman, Nagano, and Burgess-Ponnuswamy-Scheraga, the homology method of Nishikawa, the information theory method of Garnier-Osguthorpe-Robson, and the artificial neural network approach of Qian-Sejnowski.

Using the predictive data obtained from these sources, the locations of putative coiled-coil regions within SNAP-25, VAMP-2 and syntaxin were identified. These regions are shown in FIGS. 6A–C as raised curves.

The invention having been fully described, modifications within its scope will be apparent to those of ordinary skill in the art. All such modifications are within the scope of the invention.

SUMMARY OF SEQUENCES

SEQ.ID.NO. 1 is the full-length amino acid sequence for SNAP-25 protein.

SEQ.ID.NO. 2 is the full-length amino acid sequence for VAMP-2 protein.

SEQ.ID.NO. 3 is the full-length amino acid sequence for syntaxin protein.

SEQ.ID.NO. 4 is the amino acid sequence of the substrate binding domain of SNAP-25.

SEQ.ID.NO. 5 is the amino acid sequence of the substrate binding domain of VAMP-2.

SEQ.ID.NO. 6 is the amino acid sequence of the substrate binding domain of syntaxin.

SEQ.ID.NO. 7 is the amino acid sequence of ESUP/E20h.

SEQ.ID.NO. 8 is the amino acid sequence of ESUP/E26h.

SEQ.ID.NO. 9 is the amino acid sequence of ESUP/A20h.

SEQ.ID.NO. 10 is the amino acid sequence of ESUP/A20h$^{Rd}$.

SEQ.ID.NO. 11 is the amino acid sequence of SNAP-25 (49–59).

SEQ.ID.NO. 12 is the amino acid sequence of an ESUP derived from SNAP-25.

SEQ.ID.NO. 13 is the amino acid sequence of an ESUP derived from VAMP-2.

SEQ.ID.NO. 14 is the amino acid sequence of an ESUP derived from VAMP-2.

SEQ.ID.NO. 15 is the amino acid sequence of an ESUP derived from VAMP-2.

SEQ.ID.NO. 16 is the amino acid sequence of an ESUP derived from VAMP-2.

SEQ.ID.NO. 17 is the amino acid sequence of an ESUP derived from VAMP-2.

SEQ.ID.NO. 18 is the amino acid sequence of an ESUP derived from VAMP-2.

SEQ.ID.NO. 19 is the amino acid sequence of an ESUP derived from VAMP-2.

SEQ.ID.NO. 20 is the amino acid sequence of an ESUP derived from VAMP-2.

SEQ.ID.NO. 21 is the amino acid sequence of an ESUP derived from VAMP-2.

SEQ.ID.NO. 22 is the amino acid sequence of an ESUP derived from VAMP-2.

SEQ.ID.NO. 23 is the amino acid sequence of an ESUP derived from VAMP-2.

SEQ.ID.NO. 24 is the amino acid sequence of an ESUP derived from VAMP-2.

SEQ.ID.NO. 25 is the amino acid sequence of an ESUP derived from syntaxin.

SEQ.ID.NO. 26 is the amino acid sequence of an ESUP derived from syntaxin.

SEQ.ID.NO. 27 is the amino acid sequence of an ESUP derived from syntaxin.
SEQ.ID.NO. 28 is the amino acid sequence of an ESUP derived from syntaxin.
SEQ.ID.NO. 29 is the amino acid sequence of an ESUP derived from syntaxin.

What is claimed is:

1. An isolated excitation-secretory uncoupling peptide (ESUP) for inhibiting neurotransmitter secretion from neuronal cells, consisting of the amino acid sequence of SEQ.ID.NO. 4.

2. A pharmaceutical composition comprising the peptide for inhibiting neurotransmitter secretion from neuronal cells of claim 1 and a pharmaceutically acceptable carrier.

3. An isolated excitation-secretory uncoupling peptide for inhibiting neurotransmitter secretion from neuronal cells consisting of the amino acid sequence of SEQ.ID.NO. 7.

4. A pharmaceutical composition comprising the peptide for inhibiting neurotransmitter secretion from neuronal cells of claim 3 and a pharmaceutically acceptable carrier.

5. An isolated excitation-secretory uncoupling peptide for inhibiting neurotransmitter secretion from neuronal cells consisting of the amino acid sequence of SEQ.ID.NO. 8.

6. A pharmaceutical composition comprising the peptide for inhibiting neurotransmitter secretion from neuronal cells of claim 5 and a pharmaceutically acceptable carrier.

7. An isolated excitation-secretory uncoupling peptide for inhibiting neurotransmitter secretion from neuronal cells consisting of the amino acid sequence of SEQ.ID.NO. 9.

8. A pharmaceutical composition comprising the peptide for inhibiting neurotransmitter secretion from neuronal cells of claim 7 and a pharmaceutically acceptable carrier.

9. An isolated excitation-secretory uncoupling peptide for inhibiting neurotransmitter secretion from neuronal cells consisting of the amino acid sequence of SEQ.ID.NO. 12.

10. A pharmaceutical composition comprising the peptide for inhibiting neurotransmitter secretion from neuronal cells of claim 9 and a pharmaceutically acceptable carrier.

\* \* \* \* \*